US010098346B2

(12) United States Patent
Geissler et al.

(10) Patent No.: US 10,098,346 B2
(45) Date of Patent: Oct. 16, 2018

(54) DIPHENYLIODONIUM SALTS AS SULFIDOGENESIS INHIBITORS AND ANTIMICROBIALS

(71) Applicant: Ecolab USA Inc., St. Paul, MN (US)

(72) Inventors: Brett Geissler, Richmond, TX (US); Victor V. Keasler, IV, Richmond, TX (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 15/013,595

(22) Filed: Feb. 2, 2016

(65) Prior Publication Data

US 2016/0222762 A1 Aug. 4, 2016

Related U.S. Application Data

(60) Provisional application No. 62/111,797, filed on Feb. 4, 2015.

(51) Int. Cl.
*A01N 33/18* (2006.01)
*A01N 29/04* (2006.01)
(Continued)

(52) U.S. Cl.
CPC .......... *A01N 33/18* (2013.01); *A01N 29/04* (2013.01); *A61L 2/18* (2013.01); *C09K 8/528* (2013.01);
(Continued)

(58) Field of Classification Search
CPC . C09K 8/52; C09K 8/528; C09K 8/53; C09K 8/532; E21B 43/20
See application file for complete search history.

(56) References Cited

U.S. PATENT DOCUMENTS 2,947,691 A 8/1960 Bennett et al.
3,300,375 A 1/1967 Wehner
(Continued)

FOREIGN PATENT DOCUMENTS

FR 2467547 A1 4/1981
JP 2006-232800 9/2006
(Continued)

OTHER PUBLICATIONS

International Search Report and Written Opinion dated May 17, 2016 related to PCT Application No. PCT/US2016/016052, 10 pages.
(Continued)

*Primary Examiner* — Zakiya W Bates
*Assistant Examiner* — Crystal J Miller
(74) *Attorney, Agent, or Firm* — Senniger Powers LLP

(57) ABSTRACT

The present invention generally relates to the use of diphenyliodonium salts for lowering sulfide concentrations and for preventing growth of microbes in a water injection system, a hydrocarbon extraction system, or a hydrocarbon production system. Treating oilfield injection and produced fluids containing high levels of microbes with diphenyliodonium salts can significantly decrease the amount of hydrogen sulfide produced, which can be used to measure sulfidogenesis. The treatment can also decrease the number of microbes in the injection and produced fluids. Thus, these diphenyliodonium salts can be effectively used as inhibitors of hydrogen sulfide generation and as biocides in oilfield fluids.

20 Claims, 3 Drawing Sheets

(51) Int. Cl.
*E21B 43/20* (2006.01)
*A61L 2/18* (2006.01)
*C09K 8/54* (2006.01)
*C09K 8/532* (2006.01)
*C09K 8/528* (2006.01)

(52) U.S. Cl.
CPC ............... *C09K 8/532* (2013.01); *C09K 8/54* (2013.01); *E21B 43/20* (2013.01); *C09K 2208/20* (2013.01)

(56) References Cited

U.S. PATENT DOCUMENTS

| | | | |
|---|---|---|---|
| 4,864,075 A | 9/1989 | Thompson et al. | |
| 6,214,777 B1* | 4/2001 | Li | A01N 29/04 428/35.7 |
| 6,756,013 B1* | 6/2004 | Cornell | A01N 25/10 422/28 |
| 8,821,805 B2* | 9/2014 | Luo | B01J 4/002 239/398 |
| 2011/0031165 A1* | 2/2011 | Karas | C10G 29/22 208/48 AA |
| 2011/0282114 A1* | 11/2011 | Luo | B01J 4/002 585/14 |
| 2013/0004378 A1* | 1/2013 | Luo | B01J 4/002 422/129 |

FOREIGN PATENT DOCUMENTS

| | | |
|---|---|---|
| JP | 2013185017 | 9/2013 |
| WO | 01/23504 A1 | 4/2001 |

OTHER PUBLICATIONS

"Bacteria in the Oil Field" Currents in Research and Technology, The Technical Review, vol. 37, No. 1, pp. 48-53 (1989).

Uellali, Rachid et al, Antifouling activity of novel polyisoprene-based coatings made from photocurable natural rubber derived oligomers, Progress in Organic Coatings 76 (2013), pp. 1203-1214.

Crowe, Curtis W. et al., Acid Corrosion Inhibitor Adsorption and its Effect on Matrix Stimulation Results, Society of Petroleum Engineers AIME (SPE 10650) (1982), pp. 59-65.

* cited by examiner

DIPHENYLIODONIUM SALTS AS SULFIDOGENESIS INHIBITORS AND ANTIMICROBIALS

CROSS-REFERENCE TO RELATED APPLICATION

This application claims priority to U.S. Patent Application Ser. No. 62/111,797 filed on Feb. 4, 2015, the disclosure of which is incorporated herein by reference in its entirety.

FIELD OF THE INVENTION

The present invention generally relates to the use of diphenyliodonium salts for inhibiting microbial hydrogen sulfide production and preventing the growth of microbes in a hydrocarbon-containing system comprising a water injection system, a hydrocarbon extraction system, or a hydrocarbon production system.

BACKGROUND OF THE INVENTION

The introduction of sulfate- and sulfur-containing waters into oil fields for secondary oil recovery often leads to formation of undesirable sulfur-containing compounds, particularly hydrogen sulfide, by sulfur-utilizing prokaryotes. These sulfur-containing compounds lead to safety, environmental, corrosion and plugging problems, and even premature abandonment of the oil and gas field.

Particularly, hydrogen sulfide generation begins by introducing sulfate- or other sulfur-containing aqueous solutions such as seawater into an anaerobic environment for indigenous microorganisms and microorganisms contained in the introduced aqueous solutions that are capable of producing hydrogen sulfide.

Hydrogen sulfide is a toxic, corrosive, flammable gas that causes problems in both the upstream and downstream oil and gas industry. Exposure to this gas, even at low concentrations, can cause serious injury or death. Hydrogen sulfide ($H_2S$) in natural gas and crude oil reserves is often accompanied by small amounts of mercaptans (RSH), sulfides ($R_2S$), polysulfides, and carbonyl sulfide (COS). Considerable expense and effort are expended annually to reduce the $H_2S$ content of gas and oil streams to make them suitable for commercial use.

Hydrogen sulfide has an offensive odor, and natural gas and crude oil streams containing substantial amounts of $H_2S$ are considered "sour." In addition to natural gas and petroleum, there are also aqueous fluids that must be treated to reduce or remove $H_2S$, such as waste water streams. Treatments to reduce or remove $H_2S$ from hydrocarbon or aqueous streams are referred to as "sweetening" treatments because the odor of the processed products is improved by the absence of hydrogen sulfide.

In some cases, nitrate introduction has been used to prevent sulfide formation in waters because specific nitrate-reducing bacteria (NRB) are activated and use volatile fatty acids (VFAs) and the carbon dioxide from dissolved limestone in the formation to produce nitrogen and/or ammonia. Thus, the NRBs could compete with the sulfur-utilizing prokaryotes and more rapidly use the VFAs, resulting in lowered production of sulfide and sulfur-containing compounds by the sulfur-utilizing prokaryotes.

However, this nitrate treatment can cause problems if the treatment is suspended or stopped because the hydrogen sulfide production would resume at the previous concentrations or the hydrogen sulfide production could even increase due to the enhanced biomass present. Additionally, some instances of nitrate application to reduce hydrogen sulfide have increased corrosion due to the incomplete reduction of the applied nitrate. The increased amount of NRB's can also lead to injectivity issues, where the microbial population blocks the injection path of the water into the reservoir.

Thus, a need exists for an effective and efficient method to prevent the generation of hydrogen sulfide and reduce the growth of or kill the microbes responsible for the production of hydrogen sulfide in a hydrocarbon-containing system comprising a water injection system, a hydrocarbon extraction system, or a hydrocarbon production system.

SUMMARY OF THE INVENTION

One aspect of the invention is a method for reducing or preventing growth of a microbe in a hydrocarbon-containing system comprising a water injection system, a hydrocarbon extraction system, or a hydrocarbon production system. The method comprises administering an effective amount of a diphenyliodonium salt into the water injection system, the hydrocarbon extraction system, or the hydrocarbon production system.

Another aspect is a method for reducing concentration of hydrogen sulfide in a hydrocarbon-containing system comprising a water injection system, a hydrocarbon extraction system, or a hydrocarbon production system comprising administering an effective amount of a diphenyliodonium salt into the water injection system, the hydrocarbon extraction system, or the hydrocarbon production system, wherein the diphenyliodonium salt inhibits the production of hydrogen sulfide by a sulfur utilizing prokaryote.

Yet another aspect is a composition for reducing or preventing growth of a sulfur-utilizing prokaryote in a hydrocarbon-containing system comprising a water injection system, a hydrocarbon extraction system, or a hydrocarbon production system. The composition comprises an effective amount of a diphenyliodonium salt; and a solvent.

A further aspect of the invention is a composition for lowering the concentration of hydrogen sulfide in a hydrocarbon-containing system comprising a water injection system, a hydrocarbon extraction system, or a hydrocarbon production system. The composition comprises an effective amount of a diphenyliodonium salt; and a solvent.

Other objects and features will be in part apparent and in part pointed out hereinafter.

BRIEF DESCRIPTION OF THE DRAWINGS

Corresponding reference characters indicate corresponding parts throughout the drawings.

DESCRIPTION OF THE PREFERRED EMBODIMENTS

Figure 1:
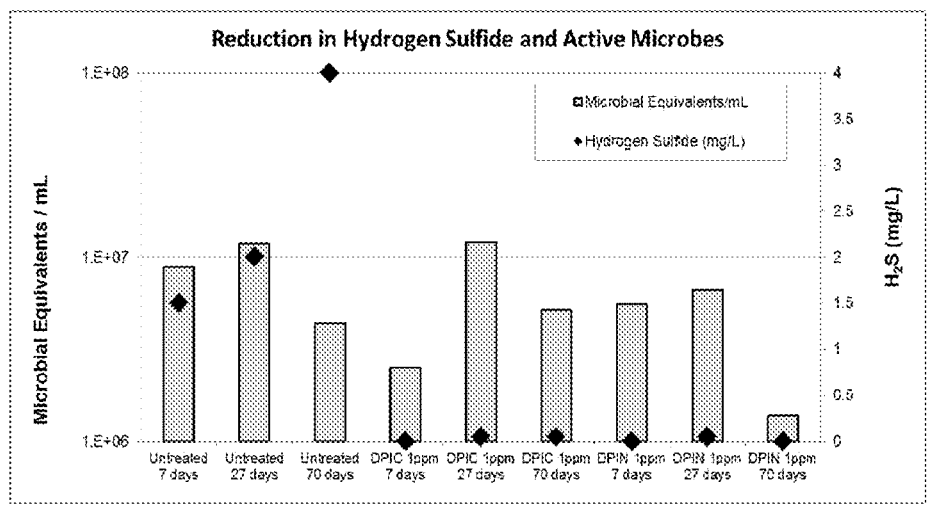
FIG. 1 is a combination bar/line graph showing the reduction in levels of active microbes and hydrogen sulfide in fluids either left untreated or treated with diphenyliodonium chloride (DPIC) or diphenyliodonium nitrate (DPIN) at 1 ppm for 7 days, 27 days, and 70 days.

The present invention is directed to methods for lowering sulfide concentrations and preventing growth of microbes in a hydrocarbon-containing system comprising a water injection system, a hydrocarbon extraction system, or a hydrocarbon production system by administering diphenyliodonium salts. Oilfield produced fluids or seawater, where each contain high levels of microbes, can be treated with diphenyliodonium salts that can significantly decrease the amount of microbes and their activity in the fluids. The treatment can also significantly decrease the amount of hydrogen sulfide produced. Thus, these diphenyliodonium salts can be effectively used as sulfidogenesis inhibitors and biocides in oilfield fluids.

One aspect of the invention is a method for reducing or preventing growth of a microbe in a hydrocarbon-containing system comprising a water injection system, a hydrocarbon extraction system, or a hydrocarbon production system comprising administering an effective amount of a diphenyliodonium salt into the water injection system, the hydrocarbon extraction system, or the hydrocarbon production system using an injection fluid.

Another aspect of the invention is a method for lowering sulfide concentration in a hydrocarbon-containing system comprising a water injection system, a hydrocarbon extraction system, or a hydrocarbon production system comprising administering an effective amount of a diphenyliodonium salt into the water injection system, the hydrocarbon extraction system, or the hydrocarbon production system using an injection fluid, wherein the diphenyliodonium salt inhibits the production of sulfide by a sulfur utilizing prokaryote.

For the methods described herein, the hydrocarbon-containing system can comprise a hydrocarbon extraction system or a hydrocarbon production system.

For the methods described herein, the water injection system, the hydrocarbon extraction system, or the hydrocarbon production system can be a subterranean hydrocarbon-containing formation, a well, a pipeline, a fluid separation vessel, a floating production storage vessel, an offloading vessel, a refinery, or a storage system.

Further, the hydrocarbon extraction or the hydrocarbon production system can be a subterranean hydrocarbon-containing formation.

In the methods described herein, the diphenyliodonium salt can further be administered with a biocide, administered with a calcium nitrate/perchlorate agent, administered with a preservative agent, combined with a method for removing sulfate, administered with a scale inhibitor, administered with an $H_2S$ scavenger, or a combination thereof.

The diphenyliodonium salt can be administered with a biocide at the same time or from about one to about 24 hours after the biocide treatment. The biocide concentration depends on the identity of the biocide and the system conditions, and generally is administered at a concentration of from about 5 to about 200 ppm in a continuous treatment and from about 10 ppm to about 10,000 ppm, from about 25 ppm to about 5,000 ppm, from about 25 ppm to about 2,500 ppm, or from about 25 ppm to about 1,000 ppm in a batch treatment.

The biocides can include tetrakis (hydroxymethyl) phosphonium sulfate (THPS), glutaraldehyde, hypochlorite, 2,2-dibromo-3-nitrilopropionamide, 2-bromo-2-nitropropane-1,3-diol, a quaternary amine, a peroxy acid, 2-propenal, 3,5-Dimethyl-1,3,5-thiadiazinane-2-thione, tributyltetradecylphosphonium chloride, cocodiamine, isothiazolinone, 4,4-dimethyloxazolidine, 1-(3-chloroallyl)-3,5,7-triaza-1-azoniaadamantane, tris(hydroxymethyl)nitromethane, a perchlorate salt, a nitrate salt, a nitrite salt, or a combination thereof.

The $H_2S$ scavenger can be monoethanolamine, diethanolamine, N-methyldiethanolamine, sodium chlorite, sodium nitrite, triazine, formaldehyde, hydrogen peroxide, 2-propenal, glyoxal, or a combination thereof.

The injection fluid can comprise seawater, produced water, fresh water, brackish water, drilling fluid, completion fluid, or a combination thereof.

The microbe can comprise a sulfur utilizing prokaryote. The sulfur utilizing prokaryote can produce hydrogen sulfide through the reduction of sulfate, thiosulfate, sulfite, bisulfite, sulfur, other inorganosulfur compounds, and organosulfur compounds, or a combination thereof.

For the methods described herein, the diphenyliodonium salt can be injected into the water injection system, hydrocarbon extraction system, or production system continuously with the injection fluid.

Further, the diphenyliodonium salt is injected into the water injection system, hydrocarbon extraction system, or production system intermittently with the injection fluid. When the diphenyliodonium salt is injected into the hydrocarbon extraction or production system intermittently, the injection of the diphenyliodonium salt is intermittently injected every one to three hours, every one to three days, or every one to three weeks.

The sulfur utilizing prokaryote can comprise a genus or species of bacteria and archaea capable of reducing sulfur compounds to produce sulfide.

Preferably, the sulfur utilizing prokaryote can comprise a sulfate-reducing bacteria. The sulfate-reducing bacteria can comprise *Petrotoga* sp., *Desulfovibrio* sp., *Oceanotoga* sp., *Desulfocurvus* sp., *Desulfomicrobium* sp., *Desulfonauticus* sp., *Lawsonia* sp., *Kosmotoga* sp., or a combination thereof.

Another aspect of the invention is a composition for reducing or preventing growth of a sulfur utilizing prokaryote in a hydrocarbon-containing system comprising a water injection system, a hydrocarbon extraction system, or a hydrocarbon production system, the composition comprising: an effective amount of a diphenyliodonium salt; and a solvent.

Yet another aspect of the invention is a composition for lowering hydrogen sulfide concentration in a hydrocarbon-containing system comprising a water injection system, a hydrocarbon extraction system, or a hydrocarbon production system, the composition comprising: an effective amount of a diphenyliodonium salt; and a solvent.

For the methods and compositions described herein, the diphenyliodonium salt can be diphenyliodonium chloride, diphenyliodonium nitrate, diphenyliodonium bromide, diphenyliodonium iodide, diphenyliodonium hexafluorophosphate, diphenyliodonium perchlorate, diphenyliodonium hexafluoroarsenate, or a combination thereof. Preferably, the diphenyliodonium salt can be diphenyliodonium chloride, diphenyliodonium nitrate, or a combination thereof. More preferably, the diphenyliodonium salt can comprise diphenyliodonium chloride or alternatively, the diphenyliodonium salt can comprises diphenyliodonium nitrate.

The diphenyliodonium salts are commercially available, for example, from Sigma-Aldrich, St. Louis, Mo., and Alfa Aesar, Ward Hill, Mass.

The effective amount of the diphenyliodonium salt is from about 1 to about 500 ppm, from about 1 to about 400 ppm, from about 1 to about 300 ppm, or from about 1 to about 200 ppm based on the total amount of injection fluid injected into the formation or production system, depending on the amount of bacteria and archaea that are present. Preferably, the effective amount of the diphenyliodonium salt is from about 1 to about 100 ppm based on the total amount of injection fluid injected into the formation or production system. More preferably, the effective amount of the diphenyliodonium salt is from about 1 to about 50 ppm based on the total amount of injection fluid injected into the formation or production system. Most preferably, the effective amount of the diphenyliodonium salt is from about 1 to about 10 ppm based on the total amount of water injected into the formation or production system.

For the compositions of the invention, the solvent can comprise water, ethanol, methanol, isopropanol, heavy aromatic naphtha, ethylene glycol monobutyl ether (EGMBE), 2-ethanol hexanol, toluene, hexane, acetic acid, ascorbic acid, formic acid, oxalic acid, or a combination thereof.

Having described the invention in detail, it will be apparent that modifications and variations are possible without departing from the scope of the invention defined in the appended claims.

EXAMPLES

The following non-limiting examples are provided to further illustrate the present invention.

Example 1: Diphenyliodonium Efficacy Tests

Figure 2:
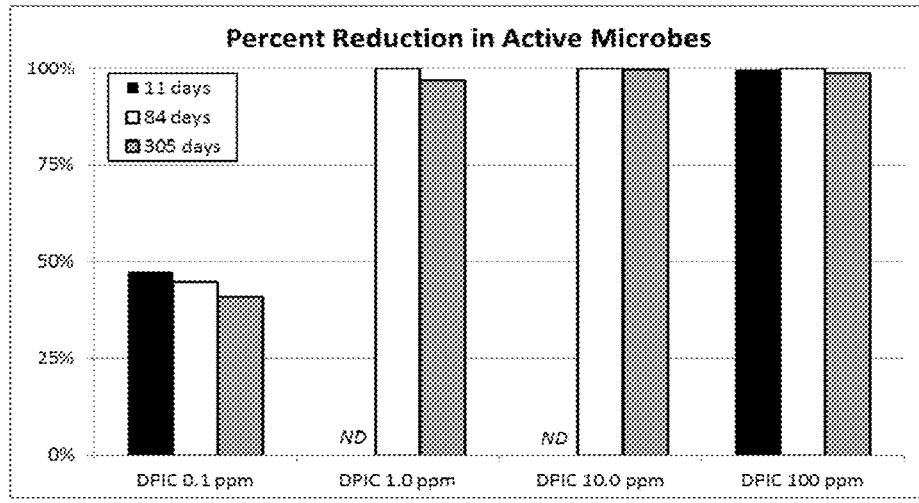
FIG. 2 is a bar graph of the percent reduction in active microbes for diphenyliodonium chloride (DPIC) at 0.1 ppm, 1 ppm, 10 ppm, and 100 ppm at 11 days, 84 days, and at 305 days.
Figure 3:
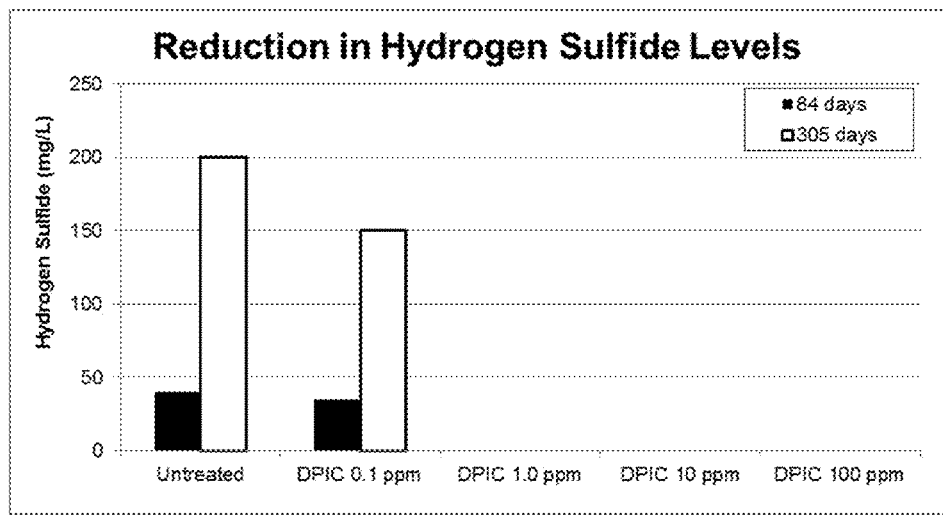
FIG. 3 is a bar graph of the reduction of hydrogen sulfide concentrations for diphenyliodonium chloride (DPIC) at 0.1 ppm, 1 ppm, 10 ppm, and 100 ppm for 84 days and 305 days.
Figure 4:
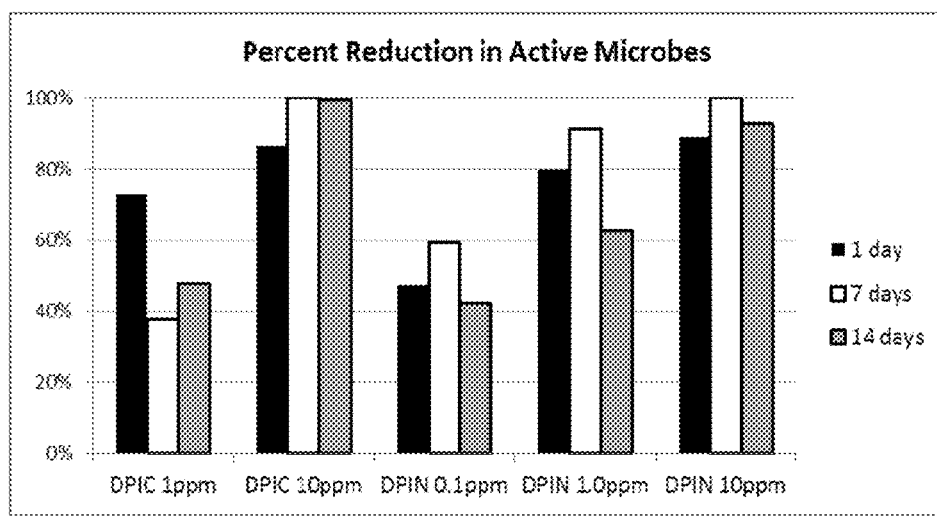
FIG. 4 is a bar graph of the percent reduction in active microbes for diphenyliodonium chloride (DPIC) at 1 ppm and 10 ppm and diphenyliodonium nitrate (DPIN) at 0.1 ppm, 1 ppm, and 10 ppm at 1 day, 7 days, and 14 days.
Figure 5:
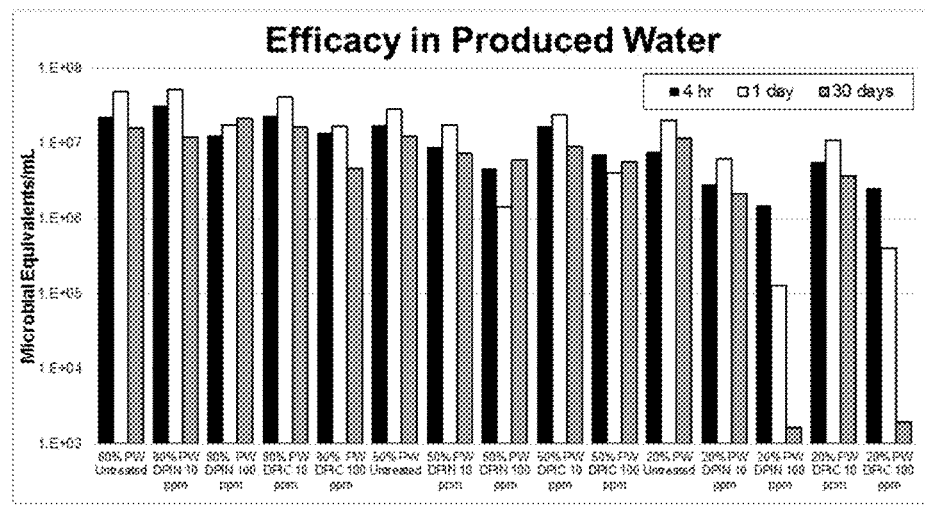
FIG. 5 is a bar graph of the efficacy of diphenyliodonium chloride (DPIC) at 10 ppm and 100 ppm and diphenyliodonium nitrate (DPIN) at 10 ppm and 100 ppm for 20%, 50%, and 80% concentrations of process water.

A hydrogen sulfide test kit (HACH, Model HS-C) and an AccuCount test kit (available from Nalco Champion) were used to test the efficacy of diphenyliodonium chloride (DPIC) and diphenyliodonium nitrate (DPIN) in 100 mL aliquots of injection water collected by mixing synthetic seawater, produced water from an oil and gas production facility off-shore California, USA, lactate, and thiosulfate. The results of the testing of these two compounds at 7, 27, and 70 days at a concentration of 1 ppm are shown in FIG. 1. The results of the testing of DPIC at 11 days, 84 days, and 305 days at concentrations of 0.1 ppm, 1 ppm, 10 ppm, and 100 ppm are shown in FIG. 2. The results of the testing of DPIC at 84 days and 305 days at concentrations of 0.1 ppm, 1 ppm, and 10 ppm are shown in FIG. 3. The results of the testing of DPIC and DPIN at 1 day, 7 days, and 14 days at concentrations of 0.1 ppm, 1 ppm, and 10 ppm in synthetic seawater are shown in the FIG. 4. The results of testing of DPIC and DPIN at 4 hours, 1 day, and 30 days at concentrations of 10 ppm and 100 ppm in 80% produced water, 50% produced water, and 20% produced water are shown in FIG. 5. The levels of hydrogen sulfide and the percentage reduction of active microbes show that both DPIC and DPIN are effective at reducing the concentration hydrogen sulfide and the level of active microbes in the samples.

Figure 6:
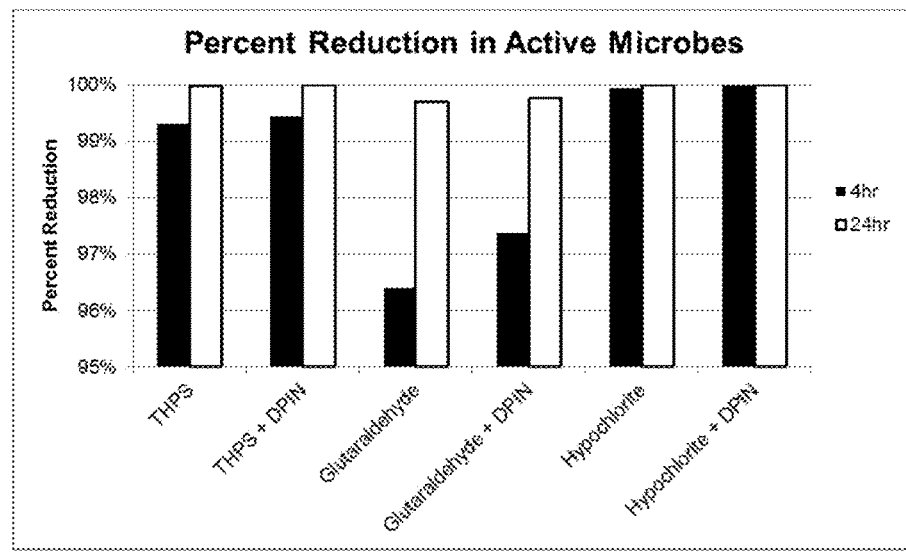
FIG. 6 is a bar graph of the efficacy of three different biocides commonly used in oil and gas systems at 4 hours and 24 hours without or with diphenyliodonium nitrate (DPIN) at 10 ppm. Tetrakis(hydroxymethyl) phosphonium sulfate (THPS) was added at 400 ppm; glutaraldehyde was added at 250 ppm; hypochlorite was added at 100 ppm.

FIG. 6 shows the percent reduction in active microbes for DPIN with tetrakis(hydroxymethyl)phosphonium sulfate (THPS) (400 ppm), glutaraldehyde (250 ppm), and hypochlorite (100 ppm). The administration of the DPIN and the other biocides was concurrent in a batch treatment.

Table 1 shows the relative abundance of each genus identified by Next-generation DNA sequencing from either the untreated or the 1 ppm DPIC treated samples after 305 days. The untreated sample after 305 days of incubation was predominated by sulfur reducing prokaryotes, with greater than 97% of the total population showing a sulfur reducing metabolism. In contrast, the same sample treated with DPIC at 305 days showed no detectable sulfur reducing prokaryotes by DNA sequencing, demonstrating that the DPIC treatment prevented growth of those organisms.

TABLE 1

| Genus Identified | Relative Abundance | Metabolic Class |
|---|---|---|
| Untreated - 305 Days | | |
| Petrotoga sp. | 39.9% | SRB |
| Desulfovibrio sp. | 33.1% | NRB/SRB |
| Oceanotoga sp. | 8.5% | SRB |
| Desulfocurvus sp. | 8.5% | SRB |
| Desulfomicrobium sp. | 3.1% | SRB |
| Desulfonauticus sp. | 1.5% | SRB |
| Lawsonia sp. | 1.0% | SRB |
| Kosmotoga sp. | 1.0% | SRB |
| Anaerophaga sp. | 0.8% | APB |
| Bellilinea sp. | 0.7% | APB |
| Desulfocella sp. | 0.4% | SRB |
| Sulfurospirillum sp. | 0.3% | NRB/SRB |
| Geoalkalibacter sp. | 0.2% | SRB/IRB |
| Prolixibacter sp. | 0.2% | APB |
| Sulfurimonas sp. | 0.2% | SOB |
| Arcobacter sp. | 0.2% | NRB/SOB |
| Dethiosulfovibrio sp. | 0.2% | SRB |
| Desulfonatronospira sp. | 0.1% | SRB |
| DPIC 1 ppm - 305 Days | | |
| Thermovirga sp. | 0.1% | SRB |
| Serratia sp. | 59.3% | NRB/GHB |
| Raoultella sp. | 28.8% | APB |
| Shimwellia sp. | 6.7% | APB |
| Kluyvera sp. | 3.5% | APB/GHB/NRB |
| Pseudomonas sp. | 0.5% | NRB/GHB |
| Proteiniphilum sp. | 0.3% | APB |
| Citrobacter sp. | 0.3% | APB |
| Mangrovibacter sp. | 0.2% | NRB |
| Sphaerochaeta sp. | 0.2% | APB |
| Acholeplasma sp. | 0.2% | APB |
| Cryptanaerobacter sp. | 0.1% | APB |

When introducing elements of the present invention or the preferred embodiments thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description and shown in the accompanying drawings shall be interpreted as illustrative and not in a limiting sense.

What is claimed is:

1. A method for reducing or preventing growth of a microbe in a hydrocarbon-containing system comprising a water injection system, a hydrocarbon extraction system, or a hydrocarbon production system comprising administering an effective amount of a diphenyliodonium salt into the water injection system, the hydrocarbon extraction system, or the hydrocarbon production system.

2. The method of claim 1 wherein the diphenyliodonium salt is administered by injecting an injection fluid into the hydrocarbon extraction system or the hydrocarbon production system.

3. The method of claim 1 wherein the hydrocarbon extraction system or the hydrocarbon production system is a subterranean hydrocarbon-containing formation, a well, a pipeline, a fluid separation vessel, a floating production storage vessel, an offloading vessel, a refinery, or a storage system.

4. The method of claim 3 wherein the hydrocarbon extraction system or the hydrocarbon production system is a subterranean hydrocarbon-containing formation.

5. The method of claim 1 further comprising administering a biocide, administering a calcium nitrate/perchlorate agent, removing sulfate, administering a preservative agent, or a combination thereof.

6. The method of claim 1 wherein the injection fluid comprises seawater, produced water, fresh water, brackish water, drilling fluid, completion fluid, or a combination thereof.

7. The method of claim 1 wherein the microbe comprises a sulfur utilizing prokaryote.

8. The method of claim 1 wherein the diphenyliodonium salt is injected into the water injection system, the hydrocarbon extraction system, or the hydrocarbon production system continuously with the injection fluid.

9. The method of claim 1 wherein the diphenyliodonium salt is injected into the water injection system, the hydrocarbon extraction system, or the hydrocarbon production system intermittently with the injection fluid.

10. A method for reducing concentration of hydrogen sulfide in a hydrocarbon-containing system comprising a water injection system, a hydrocarbon extraction system, or a production system comprising administering an effective amount of a diphenyliodonium salt into the water injection system, the hydrocarbon extraction system, or the hydrocarbon production system, wherein the diphenyliodonium salt inhibits the production of hydrogen sulfide by a sulfur utilizing prokaryote by reducing or preventing growth of the sulfur-utilizing prokaryote.

11. The method of claim 10 wherein the sulfur utilizing prokaryote produces sulfide through reduction of sulfate, thiosulfate, sulfur, bisulfite, an organosulfur compound, or a combination thereof.

12. The method of claim 10 wherein the diphenyliodonium salt is diphenyliodonium chloride, diphenyliodonium nitrate, diphenyliodonium bromide, diphenyliodonium iodide, diphenyliodonium hexafluorophosphate, diphenyliodonium perchlorate, diphenyliodonium hexafluoroarsenate, or a combination thereof.

13. The method of claim 12 wherein the diphenyliodonium salt is diphenyliodonium chloride, diphenyliodonium nitrate, or a combination thereof.

14. The method of claim 12 wherein the diphenyliodonium salt comprises diphenyliodonium chloride.

15. The method of claim 12 wherein the diphenyliodonium salt comprises diphenyliodonium nitrate.

16. The method of claim 10 wherein the effective amount of the diphenyliodonium salt is from about 1 to about 500 ppm based on the total amount of injection fluid injected into the formation or production system.

17. The method of claim 16 wherein the effective amount of the diphenyliodonium salt is from about 1 to about 100 ppm based on the total amount of injection fluid injected into the formation or production system.

18. The method of claim 16 wherein the effective amount of the diphenyliodonium salt is from about 1 to about 50 ppm based on the total amount of injection fluid injected into the formation or production system.

19. The method of claim 16 wherein the effective amount of the diphenyliodonium salt is from about 1 to about 10 ppm based on the total amount of water injected into the formation or production system.

20. The method of claim 10 wherein the hydrocarbon-containing system is a hydrocarbon extraction system, or a hydrocarbon production system.

* * * * *